(12) United States Patent
Yang

(10) Patent No.: US 10,561,751 B1
(45) Date of Patent: Feb. 18, 2020

(54) STERILIZATION ASSEMBLY OF MOBILE DEVICE

(71) Applicants: Fu Tai Hua Industry (Shenzhen) Co., Ltd., Shenzhen (CN); HON HAI PRECISION INDUSTRY CO., LTD., New Taipei (TW)

(72) Inventor: Yong-Xing Yang, Shenzhen (CN)

(73) Assignees: Fu Tai Hua Industry (Shenzhen) Co., Ltd., Shenzhen (CN); HON HAI PRECISION INDUSTRY CO., LTD., New Taipei (TW)

( * ) Notice: Subject to any disclaimer, the term of this patent is extended or adjusted under 35 U.S.C. 154(b) by 0 days.

(21) Appl. No.: 16/394,367

(22) Filed: Apr. 25, 2019

(30) Foreign Application Priority Data

Mar. 19, 2019 (CN) .......................... 2019 1 0207987

(51) Int. Cl.
*A61L 2/28* (2006.01)
*A61L 2/12* (2006.01)
*H04M 1/17* (2006.01)

(52) U.S. Cl.
CPC ................. *A61L 2/12* (2013.01); *H04M 1/17* (2013.01); *A61L 2202/11* (2013.01); *A61L 2202/14* (2013.01); *H04M 2250/12* (2013.01)

(58) Field of Classification Search
CPC .... H04M 1/17; A61L 2/10; A61L 9/20; A61L 2202/14; A61L 2/28; F25D 3/04; F25D 3/00; G05D 23/00; C12Q 1/22
USPC ............ 455/556.1; 250/461.1, 461.2; 435/31
See application file for complete search history.

(56) References Cited

U.S. PATENT DOCUMENTS

| | | | | |
|---|---|---|---|---|
| 5,830,683 | A * | 11/1998 | Hendricks | A61L 2/28 435/31 |
| 8,779,391 | B2 * | 7/2014 | Flaherty | A61L 2/10 15/339 |
| 9,750,830 | B2 * | 9/2017 | Shur | A61L 2/10 |
| 2007/0160494 | A1 * | 7/2007 | Sands | A61L 2/07 422/26 |
| 2015/0282716 | A1 * | 10/2015 | Smeltzer | G01N 33/569 600/431 |
| 2016/0289729 | A1 * | 10/2016 | Richards | B01L 3/527 |
| 2017/0080117 | A1 * | 3/2017 | Gordon | A61L 2/0052 |
| 2018/0049725 | A1 * | 2/2018 | Jones | A61B 10/0045 |

* cited by examiner

*Primary Examiner* — Congvan Tran
(74) *Attorney, Agent, or Firm* — ScienBiziP, P.C.

(57) ABSTRACT

A sterilization assembly of a mobile device includes a bacteria detection device, a microwave sterilization device, and a processor. The bacteria detection device detects a bacterial count on the mobile device by emitting light waves and receiving reflected light waves and analyzing a wavelength change in the reflected light waves. The microwave sterilization device emits microwaves to kill the bacteria. The processor sends a detection signal to the bacteria detection device to control the bacteria detection device to detect the bacterial count, and sends a sterilization signal to the microwave sterilization device to control the microwave sterilization device to emit the microwaves. The bacteria detection device sends detection feedback information to the processor. The microwave sterilization device sends sterilization feedback information to the processor.

14 Claims, 5 Drawing Sheets

| Sterilization settings |
|---|
| Sterilization value |
| Default value ○ |
| Input value ▭ Thousand |
| Bacteria detection mode |
| Manual ○ |
| Automatic |
| Daily ○ |
| Weekly ○ |
| ... |
| Sterilization mode ▭ |
| Sterilization mode |
| Manual ○ |
| Automatic ○ |

FIG. 4

STERILIZATION ASSEMBLY OF MOBILE DEVICE

FIELD

The subject matter herein generally relates to mobile devices, and more particularly to a sterilization assembly for sterilizing a surface of a mobile device.

BACKGROUND

Outer surfaces of mobile devices may become dirty easily. Currently, mobile devices do not have self-cleaning functions. A surface of a mobile device is cleaned by spaying disinfectant on the mobile device. The disinfectant may damage a screen of the mobile device and carrying a bottle of disinfectant may be inconvenient.

BRIEF DESCRIPTION OF THE DRAWINGS

Implementations of the present disclosure will now be described, by way of embodiments, with reference to the attached figures.

FIG. 4 is a diagram of an interface for configuring sterilization settings.

DETAILED DESCRIPTION

Figure 1:
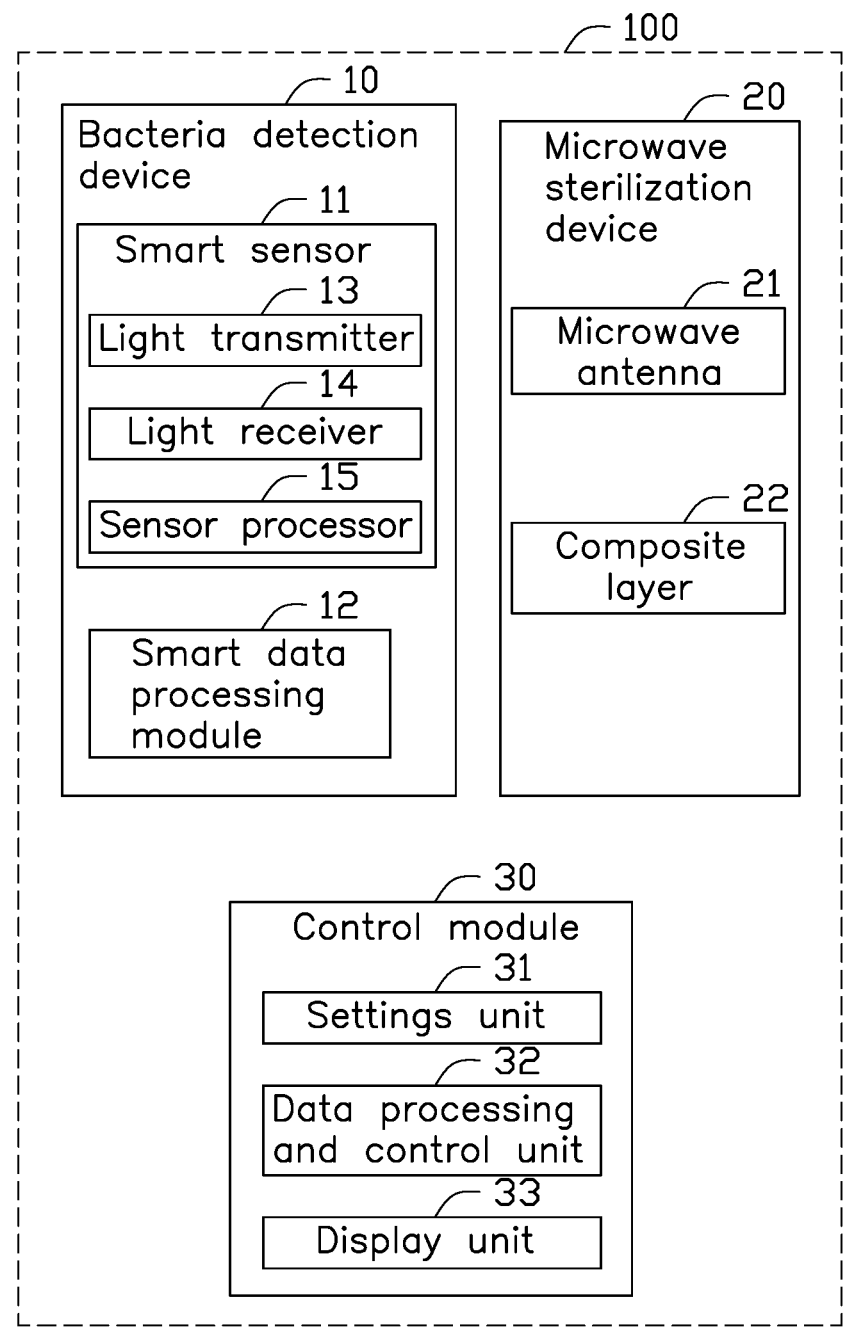
FIG. 1 is a block diagram of an embodiment of a sterilization assembly.

It will be appreciated that for simplicity and clarity of illustration, where appropriate, reference numerals have been repeated among the different figures to indicate corresponding or analogous elements. Additionally, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "comprising" means "including, but not necessarily limited to"; it specifically indicates open-ended inclusion or membership in a so-described combination, group, series and the like.

In general, the word "module" as used hereinafter refers to logic embodied in hardware or firmware, or to a collection of software instructions, written in a programming language such as, for example, Java, C, or assembly. One or more software instructions in the modules may be embedded in firmware such as in an erasable-programmable read-only memory (EPROM). It will be appreciated that the modules may comprise connected logic units, such as gates and flip-flops, and may comprise programmable units, such as programmable gate arrays or processors. The modules described herein may be implemented as either software and/or hardware modules and may be stored in any type of computer-readable medium or other computer storage device.

Figure 3:
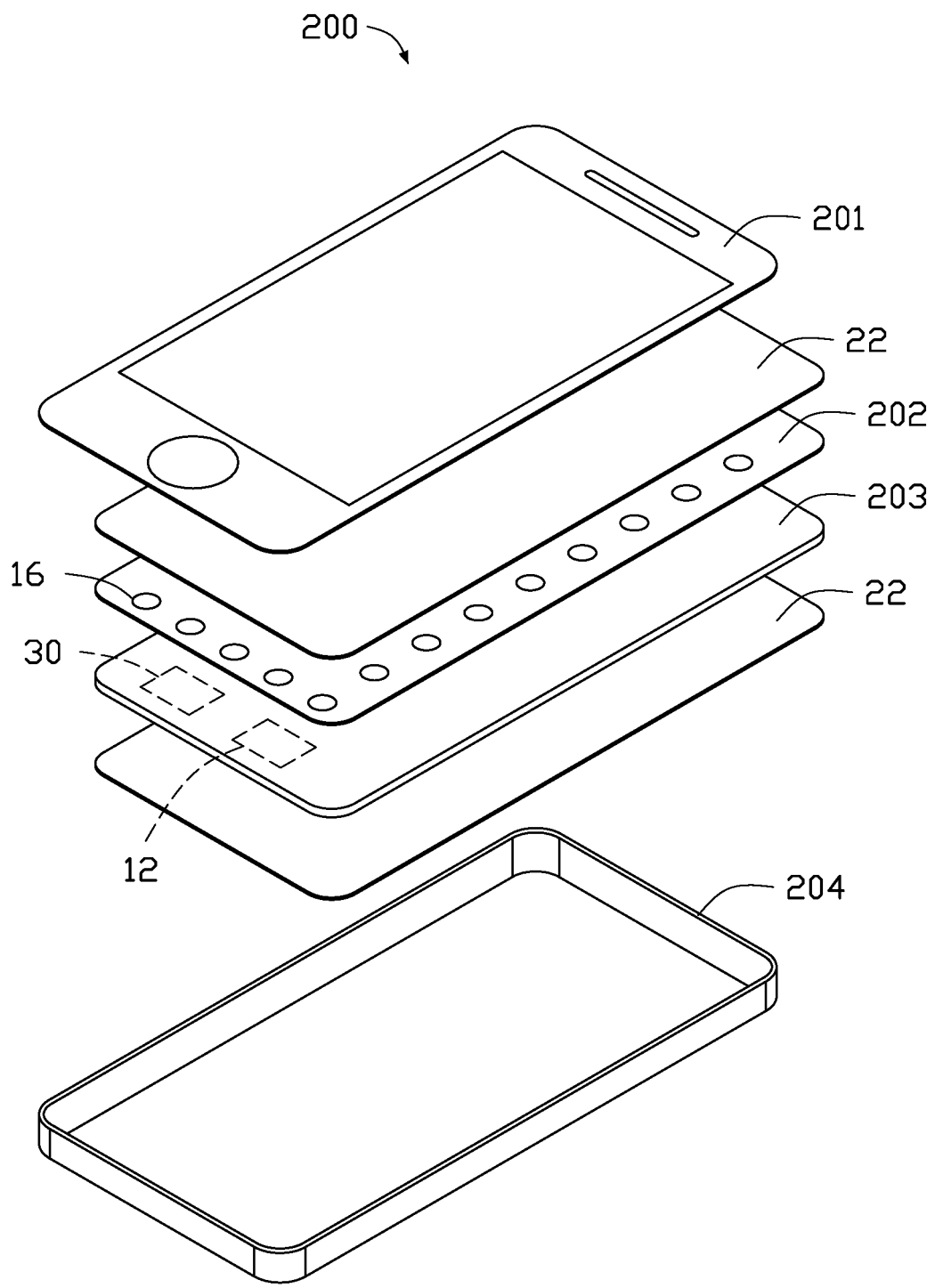
FIG. 3 is an isometric exploded view of a mobile device.

FIG. 1 shows a block diagram of an embodiment of sterilization assembly 100, which is configured to sterilize a mobile device 200 (shown in FIG. 3). The sterilization assembly 100 includes a bacteria detection device 10, a microwave sterilization device 20, and a processor 30.

In one embodiment, the mobile device 200 may be a mobile phone, a tablet computer, or the like.

The bacteria detection device 10 is configured to detect a bacterial count on the mobile device 200. The bacteria detection device 10 detects the bacterial count, after receiving a detection signal from the processor 30, by emitting light waves and receiving reflected light waves and analyzing a wavelength change of the light waves to detect the bacterial count. The bacteria detection device 10 sends detection feedback information to the processor 30.

The microwave sterilization device 20 is configured to perform sterilization according to a sterilization signal received from the processor 30. The microwave sterilization device 20 emits microwaves, and heat energy converted from the microwaves kills the bacteria to complete sterilization. The microwave sterilization device 20 sends sterilization feedback information to the processor 30.

The processor 30 is configured to set sterilization settings, control bacterial detection and sterilization, and display corresponding information on a display module of the mobile device 200. When the detected bacterial count is greater than or equal to a sterilization value in the sterilization settings, the processor 30 prompts a user to initiate manual sterilization or automatic sterilization.

As shown in FIG. 1, the bacteria detection device 10 includes a smart sensor 11 and a smart data processing module 12. The smart sensor 11 includes a light transmitter 13, a light receiver 14, and a sensor processor 15. The sensor processor 15 is integrated with the smart sensor 11. In other embodiments, the sensor processor 15 can be separately coupled to the smart sensor 11.

In one embodiment, the light transmitter 13 emits light waves which are reflected by bacteria, and the light receiver 14 receives the light waves reflected by the bacteria. Wavelengths of the received light waves may be different than wavelengths of the emitted light waves because of diffuse reflection by bacteria. The sensor processor 15 detects a wavelength change in the received light waves and sends the wavelength change to the smart data processing module 12. The smart data processing module 12 analyzes the wavelength change to detect the bacterial count and sends the detection feedback information to the processor 30.

The smart data processing module 12 is mounted on a motherboard 203 of the mobile device 200.

As shown in FIG. 1, the microwave sterilization device 20 includes a microwave antenna 21 and a composite layer 22. The microwave antenna 21 is configured to emit microwaves.

The composite layer 22 absorbs microwaves and converts the microwaves into heat, and then transfers the heat to an outer glass panel 201 (shown in FIG. 3) and a housing 204 (shown in FIG. 3) of the mobile device 200 to kill bacteria.

Figure 2:
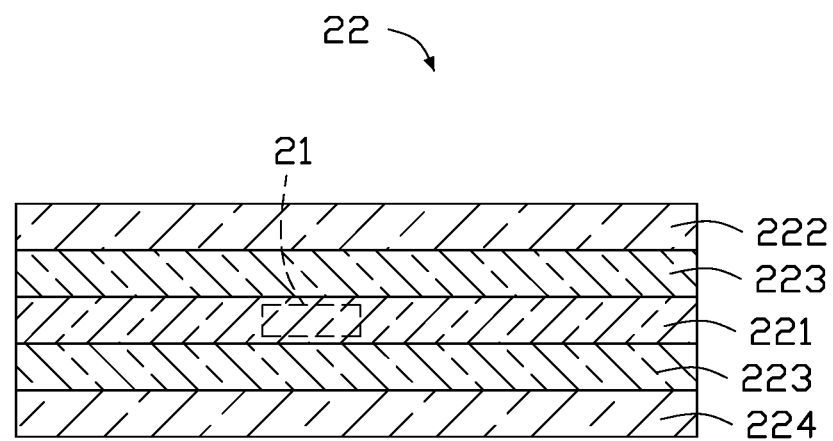
FIG. 2 is a cross-sectional diagram of a composite layer of the sterilization assembly in FIG. 1.

The composite layer 22 is transparent. As shown in FIG. 2, the composite layer 22 includes a base layer 221, two shielding layers 223 respectively arranged on opposite surfaces of the base layer 221, a heat conducting layer 222 arranged on one of the shielding layer 223, and a heat insulation layer 224 arranged on the other shielding layer 223.

The base layer 221 absorbs the microwaves and converts the microwaves into heat. The base layer 221 has a high absorption rate for microwaves within a narrow wavelength, so that the base layer 221 only absorbs microwaves of a specific wavelength and does not absorb electromagnetic waves of other wavelengths. Thus, the base layer 221 does not absorb light waves emitted by the bacteria detection device 10. The base layer 221 is made of wave-absorbing material, which includes carbon-based wave-absorbing material, iron-based wave-absorbing material, ceramic wave-absorbing material, and other materials such as conductive polymers, left-handed chiral molecules, and ions. The carbon-based wave-absorbing material includes graphene, graphite, carbon black, carbon fiber, and carbon nanotubes. The iron-based wave-absorbing material includes ferrite and magnetic iron nano-materials. The ceramic wave-absorbing material includes silicon carbide. In one embodiment, the microwave antenna 21 is integrally arranged in the base layer 221.

The shielding layer 223 shields unabsorbed microwaves within the base layer 221. The shielding layer 223 is made of shielding material, which may be a reflective type or an absorption type according to a microwave path. In one embodiment, the shielding layer 223 is made of the reflective type shielding material. The reflective type shielding material is a shielding wall composed of plate-type, sheet-type, and/or mesh-type metal to reflect scattered microwaves to attenuate microwave radiation.

The heat conducting layer 222 conducts heat converted by the base layer 221 to the outer glass panel 201 (shown in FIG. 3) and the housing 204 (shown in FIG. 3) of the mobile device 200. The heat conducting layer 222 is made of heat conductive material, which may include thermal silicone grease, thermal silica gel, a graphite gasket, a soft silicone thermal pad, phase change thermal conductive material, and the like. In one embodiment, the heat conducting layer 222 is made of a graphite gasket.

The insulating layer 224 insulates heat from conducting to a light emitting diode (LED) inner panel 202 (shown in FIG. 3) and the motherboard 203 of the mobile device 200. The heat insulation layer 224 is made of heat insulating material, which may be a porous material, a heat reflective material, or a vacuum. The porous material includes foam materials, and fiber materials. The heat reflective material includes gold, silver, nickel, aluminum foil, and metallized polyester and polyimide films. The vacuum is an internal vacuum to achieve thermal insulation.

As shown in FIG. 3, the composite layer 22 is applied in the mobile device 200. The mobile device 200 includes, arranged in sequence, the outer glass panel 201, the composite layer 22 with the heat conducting layer 222 contacting the outer glass panel 201, an LED inner screen 202 contacting the heat insulation layer 224 of the composite layer 22, the motherboard 203, a second composite layer 22 with the heat insulation layer 224 of the second composite layer 22 contacting the motherboard 203, and the housing 204 contacting the heat conducting layer 222 of the second composite layer 22.

The LED inner screen 202 includes a plurality of detection points 16. The light transmitter 13 may transmit the light waves through corresponding detection points 16, and the light receiver 14 may receive the reflected light waves through corresponding detection points 16. Thus, the light transmitter 13, the light receiver 14, and the sensor processor 15 are integrally arranged in the LED inner screen 202.

It can be understood that the heat conducting layer 222 of the two composite layers 22 respectively contact the outer glass panel 201 on a front surface of the mobile device 200 and the housing 204 on a back surface of the mobile device 200, such that the heat converted by the base layer 221 is transferred to the outer glass panel 201 and the housing 204 to kill bacteria.

It can be understood that the heat insulation layers 224 of the two composite layers 22 respectively contact the LED inner screen 202 and the motherboard 203 and do not transfer the heat converted by the base layer 221 to the LED inner screen 202 and the motherboard 203, so that normal operation of the LED inner screen 202 and the motherboard 203 is maintained.

In one embodiment, the processor 30 is arranged on the motherboard 203 (shown in FIG. 3).

As shown in FIG. 1, the processor 30 includes a settings module 31, a data processing and control module 32, and a display module 33.

As shown in FIG. 4, the settings module 31 provides an interface for configuring sterilization settings, which is displayed on the mobile device 200. The sterilization settings include a sterilization value, a bacteria detection mode, and a sterilization mode set by a user. The sterilization value is set by default or may be custom set. The sterilization value is a bacterial count.

The bacterial detection mode includes a manual detection mode and an automatic detection mode. The automatic detection mode includes a daily detection mode, a weekly detection mode, or other time period-specific detection mode set by a user. The sterilization mode includes manual sterilization mode and an automatic sterilization mode.

The data processing and control module 32 is configured to process received information, send a detection signal to the bacteria detection device 10, and send a sterilization signal to the microwave sterilization device 20.

The display module 33 is configured to control display of information on the LED inner screen 202 of the mobile device 200. Since the composite layer 22 on the LED internal screen is transparent, the information is viewable on the outer glass panel 203. For example, the sterilization value and a distribution of bacteria are displayed so that a user can judge whether sterilization is required.

Figure 5:
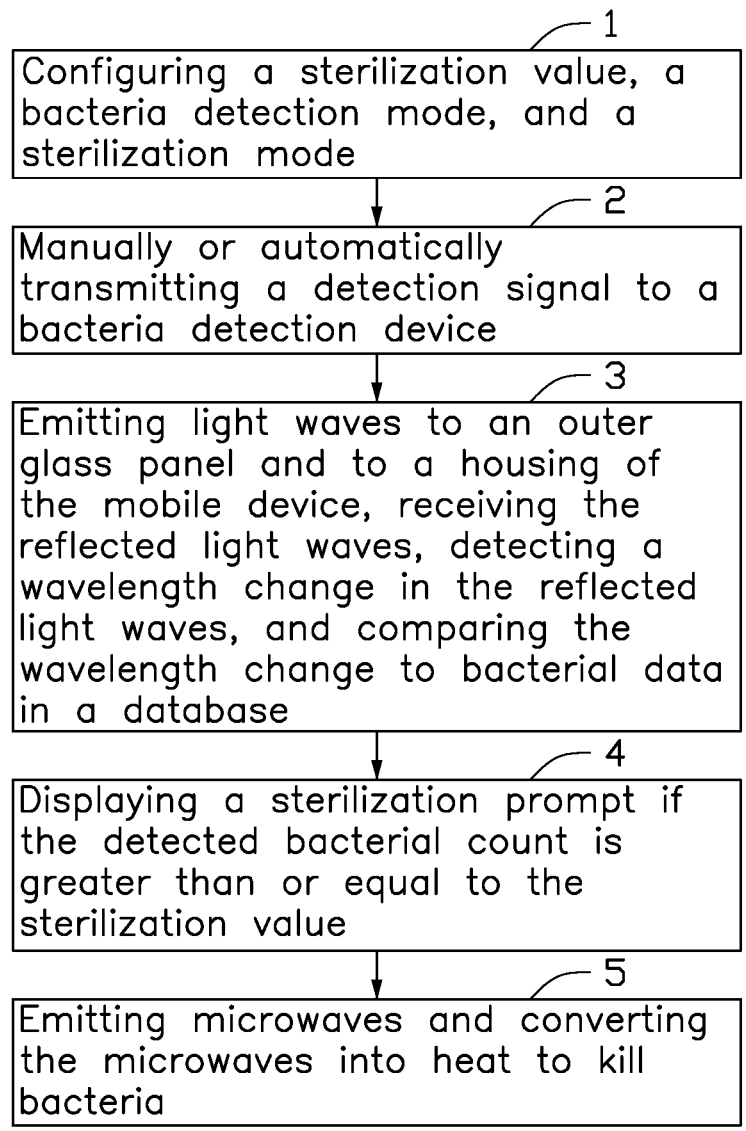
FIG. 5 is a flowchart of a sterilization method for sterilizing a mobile device.

FIG. 5 illustrates a flowchart of a sterilization method of the sterilization assembly 100. The method is provided by way of embodiment, as there are a variety of ways to carry out the method. The method described below can be carried out using the configurations illustrated in FIGS. 1-4, for example, and various elements of these figures are referenced in explaining the example method. Each block shown in FIG. 5 represents one or more processes, methods, or subroutines carried out in the example method. Furthermore, the illustrated order of blocks is by example only, and the order of the blocks can be changed. Additional blocks can be added or fewer blocks can be utilized, without departing from this disclosure.

At block 51, the sterilization value, the bacteria detection mode, and the sterilization mode are set by the settings module 31.

At block S2, a detection signal is manually or automatically transmitted to the bacteria detection device 10 through the data processing and control module 32.

At block S3, when the sensor processor 15 receives the detection signal from the processor 30, the light transmitter 13 emits light waves to the outer glass panel 201 and to the housing 204, and the light receiver 14 receives the reflected light waves. The sensor processor 15 detects a wavelength change of the reflected light waves and compares the wavelength change to bacterial data in a database to detect bacteria.

The sensor processor 15 sends detection information to the data processing and control module 32, and the data processing and control module 32 sends the detection information to the display module 33.

At block S4, if the detected bacterial count is greater than or equal to the sterilization value, the display module 33 displays a sterilization prompt, and a sterilization signal is manually or automatically sent by the data processing and control module 32 to the microwave sterilization device 20.

At block S5, after the microwave sterilization device 20 receives the sterilization signal, the microwave antenna 21 emits microwaves, the base layer 221 absorbs the microwaves and converts the microwaves into heat, and the heat is transferred to the outer glass panel 201 and the housing 204 through the heat conducting layers 222 to kill the bacteria.

After sterilization, the microwave sterilization device 20 sends sterilization feedback information to the data processing and control module 32, and the data processing and control module 32 transmits the sterilization feedback information to the display module 33. The display module 33 displays the sterilization feedback information on the LED inner screen 202, which can be viewed on the outer glass panel 203.

The sterilization method of the present disclosure can automatically sterilize the mobile device 200 without damaging the LED inner screen 202.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of shape, size and arrangement of the parts within the principles of the present disclosure up to, and including, the full extent established by the broad general meaning of the terms used in the claims.

What is claimed is:

1. A sterilization assembly of a mobile device, the sterilization assembly comprising:
    a bacteria detection device configured to detect a bacterial count on the mobile device by emitting light waves and receiving reflected light waves and analyzing a wavelength change in the reflected light waves;
    a microwave sterilization device configured to emit microwaves; and
    a processor configured to send a detection signal to the bacteria detection device to control the bacteria detection device to detect the bacterial count, and send a sterilization signal to the microwave sterilization device to control the microwave sterilization device to emit the microwaves; wherein:
    the bacteria detection device sends detection feedback information to the processor; and
    the microwave sterilization device sends sterilization feedback information to the processor.

2. The sterilization assembly of claim 1, wherein:
    the bacteria detection device comprises a smart sensor, a sensor processor, and a smart data processing module;
    the smart sensor comprises a light emitter and a light receiver;
    the light emitter is configured to emit light waves to a surface of the mobile device;
    the light receiver is configured to receive the light waves reflected by the surface of the mobile device;
    the sensor processor is configured to process the received light waves and send processed light wave data to the smart data processing module;
    the smart data processing module is configured to analyze the processed light wave data to detect the bacterial count and send the detection feedback information to the processor.

3. The sterilization assembly of claim 1, wherein:
    the microwave sterilization device comprises a microwave antenna and a composite layer;
    the microwave antenna is configured to emit microwaves;
    the composite layer is configured to absorb the microwaves, convert the microwaves into heat, and transmit the head to the surface of the mobile terminal to kill the bacteria.

4. The sterilization assembly of claim 3, wherein:
    the composite layer comprises a base layer, two shielding layers respectively arranged on opposite surfaces of the base layer, a heat conducting layer arranged on one of the shielding layers, and a heat insulation layer arranged on the other shielding layer; and
    the microwave antenna is integrally arranged in the base layer.

5. The sterilization assembly of claim 4, wherein:
    the base layer is configured to absorb the microwaves and convert the microwaves into heat;
    the shielding layers are configured to shield unabsorbed microwaves within the base layer;
    the heat conducting layer is configured to transmit heat to the surface of the mobile device;
    the heat insulation layer is configured to insulate the heat from inner components of the mobile device.

6. The sterilization assembly of claim 1, wherein:
    the processor is arranged on a motherboard of the mobile device;
    the processor is configured to configure a sterilization value, a bacteria detection mode, and a sterilization mode;
    the processor is further configured to process and analyze received feedback information, send the detection signal to the bacteria detection device, and send the sterilization signal to the microwave sterilization device;
    the processor is further configured to control the mobile device to display the feedback information.

7. The sterilization assembly of claim 6, wherein:
    the sterilization value is manually input or automatically set as a default value in an interface provided by the settings module.

8. The sterilization assembly of claim 6, wherein:
    the bacteria detection mode comprises a manual detection mode and an automatic detection mode;
    the automatic detection mode comprises a daily detection mode, a weekly detection mode, or other time period-specific detection mode;
    the sterilization mode comprises a manual sterilization mode and an automatic sterilization mode.

9. A sterilization method for sterilizing a mobile device, the sterilization method comprising:
    configuring a sterilization value, a bacteria detection mode, and a sterilization mode;
    sending a detection signal to a bacteria detection device of the mobile device;

detecting, by the bacteria detection device, a bacterial count on a surface of the mobile device and sending detection feedback information to a processor;

sending a sterilization signal to a microwave sterilization device when the bacterial count is greater than or equal to a sterilization value; and emitting, by the microwave sterilization device, microwaves and sending sterilization feedback information to the processor.

10. The sterilization method of claim 9, wherein:

the sterilization value, the bacteria detection mode, and the sterilization mode are configured in an interface provided by the processor.

11. A mobile device comprising:

an outer glass panel;

a light emitting diode (LED) inner screen;

a motherboard;

a housing; and a sterilization assembly comprising a bacteria detection device and a microwave sterilization device wherein:

the bacteria detection device is configured to detect a bacterial count on a surface of the mobile device by emitting light waves and receiving reflected light waves and analyzing a wavelength change in the reflected light waves; and the microwave sterilization device is configured to emit microwaves to kill the bacteria.

12. The mobile device of claim 11, wherein:

the microwave sterilization device comprises a two microwave antennas and two composite layers;

each of the composite layers comprises a base layer, two shielding layers respectively arranged on opposite surfaces of the base layer, a heat conducting layer arranged on one of the shielding layers, and a heat insulation layer arranged on the other shielding layer;

each of the microwave antennas is arranged in the base layer of a corresponding one of the composite layers;

the outer glass panel, a first composite layer, the LED inner screen, the motherboard, a second composite layer, and the housing are stacked in sequence.

13. The mobile device of claim 12, wherein:

the heat conducting layer of the first composite layer contacts the outer glass panel;

the LED inner screen contacts the heat insulation layer of the first composite layer;

the heat insulation layer of the second composite layer contacts the motherboard;

the housing contacts the heat conducting layer of the second composite layer.

14. The mobile device of claim 13, wherein:

the bacteria detection device comprises a light transmitter and a light receiver arranged within the LED inner screen;

the LED inner screen includes a plurality of detection points;

the light transmitter transmits light waves through corresponding detection points; and the light receiver receives the reflected light waves through corresponding detection points.

* * * * *